United States Patent [19]

Werner et al.

[11] 4,212,844
[45] Jul. 15, 1980

[54] RAPID DIAGNOSTIC COMPOSITION FOR THE DETERMINATION OF URIC ACID IN BODY FLUIDS

[75] Inventors: Wolfgang Werner, Mannheim-Vogelstang; Walter Rittersdorf, Mannheim-Waldhof, both of Fed. Rep. of Germany

[73] Assignee: Boehringer Mannheim GmbH, Mannheim, Fed. Rep. of Germany

[21] Appl. No.: 943,518

[22] Filed: Sep. 18, 1978

[30] Foreign Application Priority Data

Sep. 30, 1977 [DE] Fed. Rep. of Germany ....... 2744046

[51] Int. Cl.² .................... G01N 21/06; G01N 31/22; G01N 33/16
[52] U.S. Cl. .................................. 422/56; 23/230 B; 23/925; 252/408
[58] Field of Search ................ 23/230 B, 925; 422/56; 252/408

[56] References Cited

U.S. PATENT DOCUMENTS

| 3,528,777 | 9/1970 | Moran | 23/230 B |
| 3,822,115 | 7/1974 | Morin | 23/230 B |
| 4,072,627 | 2/1978 | Gindler | 23/230 B X |
| 4,095,948 | 6/1978 | Hunziker | 23/230 B |
| 4,141,688 | 2/1979 | Morris | 23/230 B |

*Primary Examiner*—Sidney Marantz
*Attorney, Agent, or Firm*—Sprung, Felfe, Horn, Lynch & Kramer

[57] ABSTRACT

Rapid diagnostic compositions and methods for the determination of uric acid in body fluids by inversion colorimetry, wherein the indicator used is a radical of the general formula:

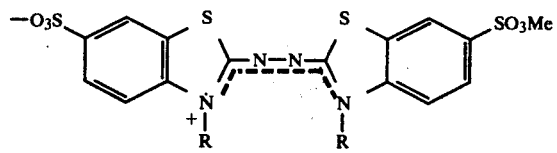

in which R is a lower alkyl radical and Me is an alkali metal atom or an ammonium group.

9 Claims, No Drawings

RAPID DIAGNOSTIC COMPOSITION FOR THE DETERMINATION OF URIC ACID IN BODY FLUIDS

The present invention relates to compositions and methods for the rapid determination of uric acid in body fluids, e.g., in blood and serum, particularly to rapid diagnostics for this purpose.

The determination of uric acid in blood or serum is of great importance for the diagnosis of gout and of other diseases in which the purine body metabolism is affected. Normally, human blood contains up to 7 mg. uric acid per 100 ml. but in the case of pathological conditions, this value can double or even treble.

A comparatively large number of quantitative wet processes are known which are essentially based upon two methods: (a) reactions in which uric acid is employed as a reducing agent, for example, the reduction of phospho-tungstic acid and colorimetric evaluation of the resultant blue coloration and (b) enzymatic determination of uric acid with uricase, the hydrogen peroxide formed oxidizing a chromogen to a colored material in the presence of peroxidase, the depth of the color produced being a measure of the concentration of the uric acid present. However, most of these processes are relatively laborious and also time-consuming since, before the reaction, all proteins present in the serum must be removed. Thus, Kageyama's test, which at present is the most exact one (Clin. Chim. Acta, 31, 421/1971) and which is based upon the enzymatic determination with uricase, requires a total analysis time of about 75 minutes.

Therefore, many attempts have been made to develop rapid diagnostics for the determination of uric acid. By rapid diagnostics, there are here meant devices which permit the desired substances to be determined quickly and without complication, for example by untrained personnel. They are usually absorbent carriers impregnated with the appropriate reagents or water-resistant films in which the reagents are incorporated. When they are dipped into the fluid to be investigated or when the fluid to be investigated is applied dropwise thereto, a color change takes place which can be evaluated, for example, by means of comparative colors.

Thus, U.S. Pat. No. 3,536,448 describes a rapid diagnostic consisting of two papers which are stuck together and covered with a protective layer. One of these papers contains ethylenediaminetetraacetic acid, sodium tungstate and hydrazine sulphate and the other one a phosphotungstate. However, this rapid diagnostic can only be used for the qualitative detection of uric acid and gives no indication of a possibly pathogenic condition.

British Patent Specification No. 1,282,089 describes a paper which contains ferric salts, persulphate and 2,4,6-tris-(2-pyridyl)-1,3,5-triazine or $2,2^1;6^1,2^{11}$-terpyridyl. It is assumed that the ferric salt forms complexes with the triazine or terpyridyl which are then reduced by uric acid to give ferrous complexes, a color change thereby taking place which is directly proportional to the uric acid concentration. However, this paper is very light-sensitive and thus not very practical.

According to published Japanese Patent Specification No. 9096-789, a paper which contains uricase and adjuvants is dipped into uric acid-containing serum. After the uricase has oxidized the uric acid to hydrogen peroxide and allantoin, this paper is pressed on to another paper which contains peroxidase and o-tolidine, the hydrogen peroxide thereby reacting with the o-tolidine to give a colored material. It is obvious that this process is laborious and, because of the necessary diffusion from one paper to another, cannot be very precise.

Whereas the above-described rapid diagnostics make use of the principle of direct colorimetric determination, in which the coloration produced is directly proportional to the concentration of the product to be measured, German Patent Specification No. 2,550,634 describes the test principle of "inverse colorimetry". For this purpose, a predetermined amount of a colored indicator is applied to a solid, inert carrier. The substance to be detected de-colorizes the indicator, the de-coloration being proportional to the amount of the substance to be determined. Exceeding the critical limiting concentration of the material to be determined can be determined very accurately by this method by the total de-colorization of an appropriate amount of the indicator.

German Patent Specification No. 2,550,634 also describes, inter alia, a rapid diagnostic for uric acid. For this purpose, glass fibre papers are impregnated with iodine, potassium iodine and starch and, by subsequent impregnation, coated with a membrane of collodion and with a second membrane of collodion and solid sodium carbonate. Uric acid-containing blood de-colorizes the iodine-starch complex and, after washing off the blood, the degree of de-colorization can be assessed. The concentration of the iodine-starch complex can be adjusted in such a manner that it corresponds precisely to the pathological amount of uric acid and thus permits a positive or negative determination. By means of further test zones with other iodine concentrations, graduated determinations can be obtained. However, although this rapid diagnostic is useful, it still suffers from considerable disadvantages, the triple impregnation being very laborious. If the second membrane is omitted, then the fluid to be investigated must first be rendered alkaline, which is laborious for the user. Furthermore, the test strips are not storage-stable because iodine disproportionates upon contact with traces of alkali.

Thus, there has been a need for a stable rapid diagnostic which is simple to produce and to use for the determination of uric acid in serum and especially in blood.

We have now, surprisingly, found that a rapid diagnostic of this type is obtained when making use of the principle of "inverse colorimetry", employing as indicator a heterocyclic azine radical of the general formula:

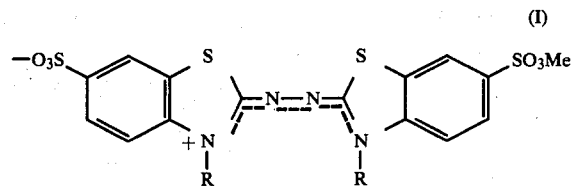

(I)

wherein R is a lower alkyl and Me is an alkali metal atom or an ammonium group.

The lower alkyl radicals are to be understood to be alkyl radicals containing up to 6 and preferably up to 4 carbon atoms, the methyl and ethyl radicals being especially preferred.

The especially preferred salts are the ammonium, lithium and sodium salts.

The radicals of general formula (I) are deep-colored compounds which are reduced by uric acid to colorless azines. In the case of a predetermined amount of radicals, the degree of decolorization is a measure of the uric acid concentration. It was not to have been foreseen that the radicals used according to the present invention could be used for the determination of uric acid with a rapid diagnostic. It was merely known that uric acid reacted in some way with radicals of general formula (I) because uric acid disturbs the oxidation of the corresponding azines to the radicals, for example in the determination of glucose in the manner described in German Patent Specifications Nos. 1,648,840 and 2,042,828; however, it was also known that this disturbance is not stoichiometric (D. Eberhardt et al., Z. klin. Chem. u. klin. Biochem., 9, 362–363/1971). Therefore, it was to have been assumed that the azines and radicals of general formula (I) would not be suitable for the quantitative determination of uric acid.

The rapid diagnostic according to the present invention can be produced in the following manner:

For a rapid test for uric acid in serum, a paper or fleece can be used as absorbent carrier. Thus, for example, filter paper can be impregnated with a radical of general formula (I), as well as with a buffer and also with adjuvants, such as wetting agents, thickeners and the like.

For a rapid test for uric acid in whole blood, the above-mentioned papers can be subsequently impregnated in organic solvents with cellulose ethers or esters in the manner described in German Patent Specification No. 1,272,019 or with waxes in the manner described in German Patent Specification No. 1,598,048. The membrane formed or the hydrophobing of the test paper then enables the blood to be washed off. However, it is preferable to incorporate the radicals of general formula (I) into water-stable films in the manner described in German Patent Specification No. 1,598,153, from which the blood then merely has to be wiped off.

The radicals of general formula (I) can be prepared in substance by oxidizing the corresponding azines with iodine, lead tetraacetate, lead dioxide or some other appropriate oxidation agent (cf., for example, Hünig, Liebigs Ann. Chem., 676, 36-51/1964). However, they can also be produced directly by these oxidation agents or by hydrogen peroxide and peroxidase in the impregnation solution. The amount of the radicals to be present in the formulations depends upon the amount of uric acid which it is desired to determine and can easily be determined empirically.

It is also preferable to add the corresponding azines to the formulations in order to prevent a possible disproportionation of the radicals.

Furthermore, such a disproportionation can also be prevented by the addition of neutral inorganic alkali metal salts, such as chloride, bromides, sulphates and the like.

As buffers, there can be used those systems which are conventional for rapid tests, for example citrate, phthalate and the like buffers. Since, under certain circumstances, when using comparatively large amounts of radicals (for comparatively high uric acid concentrations), salting out phenomena can occur, it is sometimes preferable to use lithium as the cation for the above-mentioned buffers.

The pH value of the buffer should be from 3 to 7 and preferably from 4 to 6. Higher pH values are not suitable since they can bring about a decomposition of the radicals.

The wetting agent used can be any conventional non-ionic, anionic and cationic material, for example lauryl sulphate, dioctyl sulphosuccinate, lauryl polyglycol ether, lauryl pyridinium chloride or the like.

The thickening agent used can be an alginate, a cellulose ether, carboxymethylcellulose or the like.

The synthetic resin dispersion used for the production of test films can be, for example, one of those described in German Patent Specification No. 1,598,153, polyvinyl propionate, acetate and co-polymers thereof being preferred.

The test papers or test films are produced in the usual manner, cut up into small squares (e.g. 6×6 mm.) and stuck or sealed on to rod-shaped carriers and preferably on to foils or affixed in some other appropriate manner. Test rodlets with only one test zone are outstandingly useful for measurement in simple reflection photometers or for visual comparison with comparative colors. However, it is particularly advantageous to apply to a test rodlet several test zones with increasing radical concentrations. After application of the fluid to be investigated, there is thus obtained a series of completely, partly or non-de-colorized test zones in which the equivalence point, i.e. the point at which de-colorization has just taken place, can also be readily recognised without comparative colors.

The following Examples are given for the purpose of illustrating the present invention, the following abbreviations thereby being used:

radical A = the radical of the diammonium salt of azino-bis-N-ethylbenzthiazolone-disulphonic acid;
radical B = the radical of the dilithium salt of azino-bis-N-ethylbenzthiazolone-disulphonic acid;
radical C = the radical of the dilithium salt of azino-bis-N-methylbenzthiazolone-disulphonic acid.

EXAMPLE 1

| Composition: | |
|---|---|
| polyvinyl acetate propionate dispersion | 45 g. |
| sodium alginate, 1.85% in 0.5M sodium phosphate buffer, pH 5.6 | 35 g. |
| radical A (radical content 33.8%) azino-bis-N-ethylbenzthiazolone-disulphonic acid diammonium salt } in 22 ml. water | x g. |
| | y g. |
| dioctyl sodium sulphosuccinate in 8 ml. methanol | 0.75 g. |

| formulation | a | b | c | d | e | f | g |
|---|---|---|---|---|---|---|---|
| x g. | 0.04 | 0.05 | 0.06 | 0.07 | 0.08 | 0.09 | 0.1 |
| y g. | 0.25 | 0.30 | 0.35 | 0.40 | 0.45 | 0.50 | 0.60 |

The components were thoroughly stirred up and then centrifuged for 5 minutes at 1500 r.p.m. in order to remove air bubbles. Thereafter, a 0.38 mm. thick film was coated on to a polycarbonate foil and dried for 30 minutes at 50° C. The coated materials were cut into 6 mm. wide strips and then sealed on a polyester film spaced 1 mm. apart. This film was cut up into 6 mm. wide rodlets so that test strips were obtained which contained the seven test zones a to g side by side.

Sera containing 2, 4, 6, 8 and 10 mg. uric acid per 100 ml. were then applied dropwise to the test strips and, after 5 minutes, the test strips were wiped. The following result was obtained:

TABLE 1

| serum mg./100 ml. | result |
|---|---|
| 2 | no test zone completely de-colorized |
| 4 | de-colorization of test zones a and b |
| 6 | de-colorization of test zones a to d |
| 8 | de-colorization of test zones a to f |
| 10 | de-colorization of all test zones |

The uric acid content of the serum can thus be easily estimated in the following manner:

mg. uric acid/100 ml.=number of de-colorized test zones+2.

EXAMPLE 2

| composition: | |
|---|---|
| polyvinyl acetate propionate dispersion | 45 g. |
| sodium alginate, 1.85% in 0.5M lithium citrate buffer, pH 5 | 35 g. |
| radical B (radical content 35.1%) azino-bis-N-ethylbenzthiazolone-disulphonic acid dilithium salt | 0.2 g. |
| fluorinated non-ionic wetting agent (Forafac 1110) | 0.2 g. |
| distilled water | 20 ml. |

The mass was mixed, centrifuged, coated on and dried in the manner described in Example 1. After cutting up in a manner analogous to that described in Example 1, test strips were produced which contained only one test zone.

Uric acid-containing blood was applied dropwise to the test zone, wiped off after 1 minute and measured in a commercially available reflection photometer (Reflomat). The results obtained are summarised in the following Table 2:

Table 2

| mg.% uric acid | scale division |
|---|---|
| 0 | 45 |
| 2 | 42 |
| 3 | 38.5 |
| 4 | 35 |
| 5 | 32 |
| 6 | 28 |
| 7 | 23.5 |
| 8 | 21.5 |
| 9 | 19 |
| 10 | 16 |
| 11 | 13.5 |
| 12 | 9 |

EXAMPLE 3

Filter paper (Schleicher & Schüll No. 2316) was impregnated with a solution of the following composition and then dried at 50° C.:

| | |
|---|---|
| lithium citrate buffer, pH 6, 0.5 molar | 50 ml. |
| radical C (radical content 32.5%) azino-bis-N-methylbenzthiazolone-disulphonic acid dilithium salt | 0.135 q. |
| | 0.2 g. |
| lauryl polyoxyethylene ether | 0.1 g. |
| distilled water | ad 100 ml. |

The paper was cut up into 6 mm. wide strips and stuck on to a polystyrene film by means of a transfer adhesive. This was cut up into 6 mm. wide rodlets which then had a square test zone on the lower end.

The test rodlets were dipped into uric acid-containing serum and assessed after 60 seconds. A serum containing 8 mg. uric acid/100 ml. gave a complete de-colorization whereas one with 7 mg./100 ml. still displayed a green coloration. If it is desired to have a complete de-colorization at 7 mg./100 ml., then it is necessary to use 0.155 g. of radicals, whereas for 9 mg./100 ml., 0.195 g. of radicals is necessary. Thus, in this manner, the desired threshold value can be adjusted.

EXAMPLE 4

| Composition: | |
|---|---|
| polyvinyl acetate propionate dispersion | 45 g. |
| sodium alginate, 1.5% in 0.5M aqueous ammonium bromide solution | 35 g. |
| radical A (radical content 99.5%) azino-bis-N-ethylbenzthiazolone-disulphonic acid diammonium salt | 50 mg. |
| | 0.3 g. |
| fluorinated non-ionic wetting agent | 0.2 g. |
| distilled water | 14.0 ml. |
| adjusted to pH 5 with 0.5M ammonia solution. | |

The mass was coated as a 0.3 mm. thick film which was dried for 30 minutes at 50° C. and further worked up analogously to Example 2 to give test strips with one test zone. Uric acid-containing serum was applied dropwise to the test zone, after 1 minute wiped off and after a further minute measured in a commercially available remission photometer (Zeiss, PMQ III) at 620 nm. The results obtained are summarised in the following Table 3:

TABLE 3

| mg.% uric acid | % remission |
|---|---|
| 1 | 39.9 |
| 3 | 42.1 |
| 5 | 44.1 |
| 7 | 46.2 |
| 9 | 48.4 |
| 11 | 50.8 |
| 13 | 52.6 |

It will be understood that the specification and examples are illustrative but not limitative of the present invention and that other embodiments within the spirit and scope of the invention will suggest themselves to those skilled in the art.

What is claimed is:

1. Rapid diagnostic composition for the determination of uric acid in body fluids by inversion colorimetry comprising at least one adjuvant material selected from the group consisting of buffers, wetting agents, and thickening agents and, as an indicator, a radical of the formula

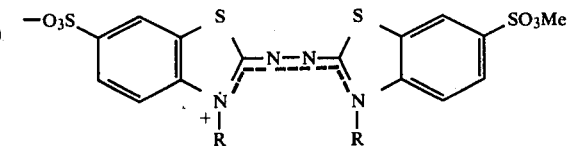

in which
R is a lower alkyl radical and
Me is an alkali metal atom or an ammonium group.

2. Rapid diagnostic composition as claimed in claim 1, also comprising the azine corresponding to said indicator radical.

3. Rapid diagnostic composition as claimed in claim 1 wherein said adjuvant material is a buffer.

4. Rapid diagnostic composition as claimed in claim 3 wherein the buffer contains lithium as the cation.

5. Rapid diagnostic composition as claimed in claim 3 wherein the pH value of the buffer is from 3 to 7.

6. Rapid diagnostic composition as claimed in claim 5, wherein the pH value of the buffer is from 4 to 6.

7. Rapid diagnostic composition as claimed in claim 1, wherein the indicator is impregnated onto an absorbent carrier.

8. Rapid diagnostic composition as claimed in claim 1, wherein the indicator is embedded in a synthetic resin film.

9. Rapid diagnostic composition as claimed in claim 1, wherein several test zones with different amounts of indicator are fixed to a carrier.

* * * * *